United States Patent [19]
Ott

[11] Patent Number: 5,433,693
[45] Date of Patent: Jul. 18, 1995

[54] NEUTRON-CAPTURE THERAPY APPARATUS AND METHOD

[76] Inventor: Karl O. Ott, 132 Glenn Ct., West Lafayette, Ind. 47906

[21] Appl. No.: 998,994

[22] Filed: Dec. 31, 1992

[51] Int. Cl.$^6$ .............................................. A61N 5/00
[52] U.S. Cl. .................................................... 600/1
[58] Field of Search ........................................ 600/1-8

[56] References Cited

PUBLICATIONS

F. S. Wheeler et al., "Reactor Physics Design for An Epithermal Neutron Beam...", 1989, pp. 69-71.
Nigg et al., "Conceptual Physics Design of an Epithermal-Neutron Facility...".
Neuman et al., "Conceptual Design of A Medical Reactor for Neutron Capture Therapy", Oct. 1990, pp. 77-92.
Mishima, "Investigation of a Nuclear Reactor for Cancer Therapy", 1990 March.
B. J. Allen et al., "Performance of the Currently Available Epithermal Neutron Beam...", 1999, pp. 53-56.
O. K. Harling et al., "Installation and Testing of an Optimized Epithermal Neutron Beam...", 1990, pp. 185-199.
Floyd J. Wheeler et al., "Epithermal Neutron Beam Design for Neutron Capture Therapy...", Oct. 1990, pp. 106-117.
David W. Nigg et al., "Demonstration of Three-Dimensional Determinstic Radiation Transport...", Jan./Feb. 1991, pp. 43-53.
Ref. 1 "Boron Neutron Capture Therapy and Radiation Synovectomy Research at the Massachusetts Insitute of Technology Research Reactor", *Nuclear Science and Engineering*, Otto K. Harling et al., vol. 110, pp. 330-348, Apr. 1992.
Ref. 2 "Possible Use of Cold Neutrons for Boron Neutron Capture Therapy", *Nuclear Science and Engineering*, M. Papaspyrou and L. E. Feinendegen, vol. 110, pp. 349-354, Apr. 1992.
"Development and Deployment of a Revolutionary Brain Tumor Treatment" Boron Neutron Cancer Therapy-University Consortium, Inc.
Excerpt from the Oct. 22, 1993 Conference Report 103-305 to House Resolution 2445 in Congress (referring to "the Department's Boron Neutron Capture Therapy" (BNCT)* Program and the BNCT-University Consortium).
"Clinical Results of Boron Neutron Capture Therapy", Progress in *Neutron Capture Therapy for Cancer*, Edited by B. J. Allen et al., Plenum Press, New York 1992 pp. 561-568.

*Primary Examiner*—William E. Kamm
*Assistant Examiner*—John P. Lacyk
*Attorney, Agent, or Firm*—Woodard, Emhardt, Naughton, Moriarty & McNett

[57] ABSTRACT

Patient treatment rooms are circularly spaced around a nuclear reactor core. Suitable shielding is provided between the rooms and the core, with neutron transmission passageways provided in the shielding from the core to provide space for appropriate collimating equipment. The core is generally cylindrical and multi-regional, with the inner two or three regions containing nuclear fuel, the inner core producing most of the fission neutrons, the first core ring containing a low enrichment fuel, and the third containing thorium or depleted uranium metal or some other heavy metal for inelastic scattering of neutrons and gamma ray absorption. Two moderator rings, each containing a different moderator liquid composition with variable thermal neutron absorbers and gamma ray absorbers, surrounding the multi-regional core. A heavy metal gamma ray shield surrounds the second moderator ring. The arrangement constricts the neutron spectrum in the reactor itself to transmit only epithermal neutrons to the patients, without the typical spectrum shaping filters normally contemplated for use between reactors and treatment subjects.

27 Claims, 3 Drawing Sheets

NEUTRON-CAPTURE THERAPY APPARATUS AND METHOD

BACKGROUND OF THE INVENTION

1. Field of the Invention

This invention relates generally to neutron-capture, primarily in boron-10, therapy (hereinafter BNCT) treatment of cancerous tumors, and more particularly to apparatus and method for conducting such therapy.

It is desirable that BNCT be accomplished effectively at a low cost of generation of neutron beams with minimal side effects such as caused by gamma ($\gamma$) rays or "thermal", "epithermal", and "fast" neutrons. Typical energy ranges of these three neutron groups are: thermal $\leq 1$ eV, epithermal 1 eV to 50 keV, fast $\geq 50$ keV.

In my view, this can be achieved by providing a low-power reactor, with patients placed close to the reactor to have adequate beam intensity, notwithstanding the low power. Neutron beam optimization over a short distance between the reactor core and the patient is then required. The neutrons emerging from the reactor/moderator assembly should already be what is needed for the BNCT.

2. Description of the Prior Art

Boron-neutron-capture therapy (BNCT) has been known as having potential for treatment of cancerous tumors for more than thirty years. In such therapy, there are two primary components, both of which need to be optimized during the development of the procedure.

The first is a chemical boron (B-10) compound which is preferentially deposited in tumors. The second is a beam of neutrons which preferentially reacts with B-10 in the tumor.

Capture of a neutron in B-10 splits the compound nucleus B-11 boron-11) into two nuclei, He-4 (helium-4) and Li-7 (lithium-7), with energies of 1.5 and 1.0 MeV, respectively. Both nuclei lose their energy over a short distance, largely within a single cell. The damage through ionization during the slowing down of these two nuclei destroys the tumor cell with a high probability. For the destroyed cell to be, again with a high probability, a cancer cell, requires the combined maximization of the preferential deposition of boron in tumors and the preferential exposure of the tumor to neutrons of the right energy.

Alternatives to boron capture are also being considered. One alternative is the fissioning of a U-235 (uranium-235) nucleus, resulting in two fission products which can also destroy the host cell.

Some background and recent thinking on the subject of BNCT are described in two articles which have recently appeared in the publication entitled *Nuclear Science and Engineering*. One of them (hereinafter referred to as "Ref. 1.") is by Otto K. Harling et al., Volume 110 (1992), pages 330-348. The other (hereinafter referred to as "Ref. 2.") is by Manfred Papaspyrou and Ludwig E. Feinendegen in Volume 110, pages 349-354. The Harling et al. article has a FIG. 1 illustration of the five megawatt Massachusetts Institute of Technology Reactor (MITR) arranged for medical therapy. The Papaspyrou/Feinendegen article describes the basic principles of BNCT, and the possible use of cold neutrons. While the Harling et al. article indicates that the reactor shown in the article is an upgraded model, I believe it is possible to provide apparatus which will make such therapy accessible to more people at less cost and with considerably lower side effects than appears possible with the MITR-II equipment, for example.

The current BNCT experimental applications by others of which I am aware do beam optimization outside of the reactor, starting with a neutron leakage spectrum, which by itself is inadequate for BNCT. A beam modifying "filter" is then applied to prepare the beam for BNCT. According to my concept, neutronics optimization is to be accomplished within the reactor vessel itself, resulting in a simpler and more compact design, while minimizing at the same time the side effects. An additional, more specific design criterion for minimizing side effects has been identified during the preparation of this application, which, to my knowledge, has not appeared in the literature in this form: the minimization of the overall number of neutrons in the beam, say $n_t$. This criterion is also considered in the conceptual design of this application.

Some additional papers, Refs. 3 to 10, also describe nuclear reactor application for BNCT. These papers are as follows:

Ref. 1 "Boron Neutron Capture Therapy and Radiation Synovectomy Research at the Massachusetts Institute of Technology Research Reactor", *Nuclear Science and Engineering*, Otto K. Harling et al., Vol 110, pgs. 330-348, Apr. 1992.

Ref. 2 "Possible Use of Cold Neutrons for Boron Neutron Capture Therapy", *Nuclear Science and Engineering*, M. Papaspyrou and L. E. Feinendegen, Vol 110, pgs. 349-354, Apr. 1992.

Ref. 3. "Performance of the Currently Available Epithermal Neutron Beam at the Massachusetts Institute of Technology Research Reactor (MITR-II)", *Progress In Neutron Capture Therapy for Cancer*, Edited by B. J. Allen et al., Plenum Press, New York, 1992, pgs. 53-56.

Ref. 4. "Installation and Testing of an Optimized Epithermal Neutron Beam at the Brookhaven Medical Research Reactor (BMRR)", R. G. Fairchild et al., *Neutron Beam, Development, and Performance for Neutron Capture Therapy*, Edited by O. K. Harling et al., Plenum Press, New York, 1990, pgs. 185-199.

Ref. 5. "Epithermal Neutron Beam Design for Neutron Capture Therapy at the Power Burst Facility and the Brookhaven Medical Research Reactor", Floyd J. Wheeler et al., *Nuclear Technology*, Vol. 92, October, 1990, pgs. 106-117.

Ref. 6. "Demonstration of three-dimensional deterministic radiation transport theory dose distribution analysis for boron neutron capture therapy", by David W. Nigget al., *Medical Physics*, Vol. 18(1), Jan/Feb 1991, pgs. 43-53.

Ref. 7. "Reactor physics design for an epithermal neutron beam at the Power Burst reactor Facility", F. J. Wheeler et al., *Strohlenther. Onkol.*, Vol. 165, 1989, pgs. 69-71.

Ref. 8. "Conceptual Physics Design of an Epithermal-Neutron Facility for Neutron Capture Therapy at the Georgia Tech Research Reactor", David W. Nigg and Floyd J. Wheeler, published by Idaho National Engineering Laboratory according to its INEL BNCT Program, under U.S. Government DOE Contract No. DE-AC07-761DO1570.

Ref. 9. "Conceptual Design of a Medical Reactor for Neutron Capture Therapy", William A. Neuman and James L. Jones, *Nuclear Technology*, Vol. 92, Oct. 1990, pgs. 77-92.

Ref. 10. "Investigation of a Nuclear Reactor for Cancer Therapy", Yutaka Mishima, Report by the Special Institute for Cancer Neutron Capture Therapy, Kobe University, Japan, March 1990.

Most of these papers describe beam preparation activities at four reactors:

MITR-II (Ref. 3; this is a different version of Ref. 1)
BMRR (Brookhaven Medical Research Reactor, Refs. 4 to 6)
PBF (Power Burst Facility, Refs. 5 and 7)
GTRR (Georgia Tech Research Reactor, Ref. 8)

Beam Optimisation at a fifth reactor (the European High Flux Reactor in Petten, Netherlands) follows the same principles; see Ref. 9, p. 78. The Ref. 9 paper describes a concept for a multiple treatment room facility associated with a reactor using a low-enriched uranium-zirconium hydrite fuel and associated filters using solid plates, non-circulating $D_2O$, and water for coolant. The concept is to provide a low power reactor and use "power cycling" such as 10 minutes at full power and 50 minutes standby at 1% power, for example. Simultaneous treatment of patients in several treatment rooms would be accomplished during all or part of the full power mode, the duration being selectable to tailor treatment to each patient's need, and controlled by beam shutters.

What all these efforts have in common is that they start with an unsuitable neutron spectrum, consisting primarily of thermal neutrons, and then employ bulky external "filters" to shape the neutron spectrum for BNCT application. The primary task of these arrangements is to "filter" out the undesirable thermal neutron and to reduce the fast neutron and $\gamma$-ray components of the leakage spectra.

SUMMARY OF THE INVENTION

Described briefly, according to a typical embodiment of the present invention, a nuclear reactor core is organized in a way to produce a source for epithermal neutrons at a high intensity. The core is generally cylindrical and preferably multi-regional. An arrangement with two regions containing nuclear fuel is described here. The inner core, with typically 20% enriched uranium, is producing most of the fission neutrons. The outer core ring contains fuel with a much lower enrichment fuel, typically 3 to 5%. In this lower enriched fuel ring begins the inelastic down-scattering of the bulk of the neutrons as well as the absorption of the $\gamma$-rays, both coming out of the inner core. The next ring consists of a heavy metal to cause both considerable additional inelastic down-scattering and $\gamma$-ray absorption. In the context of the present application, heavy metals include those having an atomic weight greater than iron. Some examples of heavy metals having a high inelastic scattering capability are tungsten (W), ruthenium (Re), lead (Pb) or bismuth (Bi). Thorium (Th) has even larger inelastic scattering capability; it has, however, the disadvantage of generating some additional fission neutrons and $\gamma$-rays as does U-238, available in the form of depleted uranium. The three inner zones are surrounded by two liquid moderator rings containing also an absorber. These two rings perform the functions of slowing down of neutrons while constricting the neutron spectrum at its low end, and further absorption of $\gamma$-rays. The shaping of the neutron spectrum in these two rings can be varied by changing the absorber concentration in the circulating liquids of these two rings. Patient treatment rooms are circularly spaced around the reactor/moderator assembly and, in one embodiment they are on two levels. The two moderator/absorber rings are sectored so that each treatment room is associated with a sector different from each other room. The different shaping of the neutron spectrum in each sector can be accomplished by changing the absorber concentration in the circulating liquids of these sectors. Suitable shielding is provided around the reactor and between the rooms, with neutron transmission passageways provided in the shielding which also allow space for appropriate collimating and focusing and shutting equipment. The neutron transmission passageways may contain different beam tube equipment. This, together with the different absorber concentration in moderating sectors, allows an optimization for different tumor depths and sizes to be treated in the different treatment rooms. The variation of the neutron spectra and their mean energy aims at an optimization for given tumor depth, whereas a variation of the passageways affects primarily the focus and the lateral spread of the beam, optimizing it for given size.

DESCRIPTION OF THE INVENTION

The principles of the invention as well as the advantages compared to other applications or designs are described and discussed on the basis of the preferred embodiment. Alternative realizations of the same principles are introduced and discussed hereafter.

BRIEF DESCRIPTION OF THE DRAWINGS OF THE PREFERRED EMBODIMENT

Figure 3:
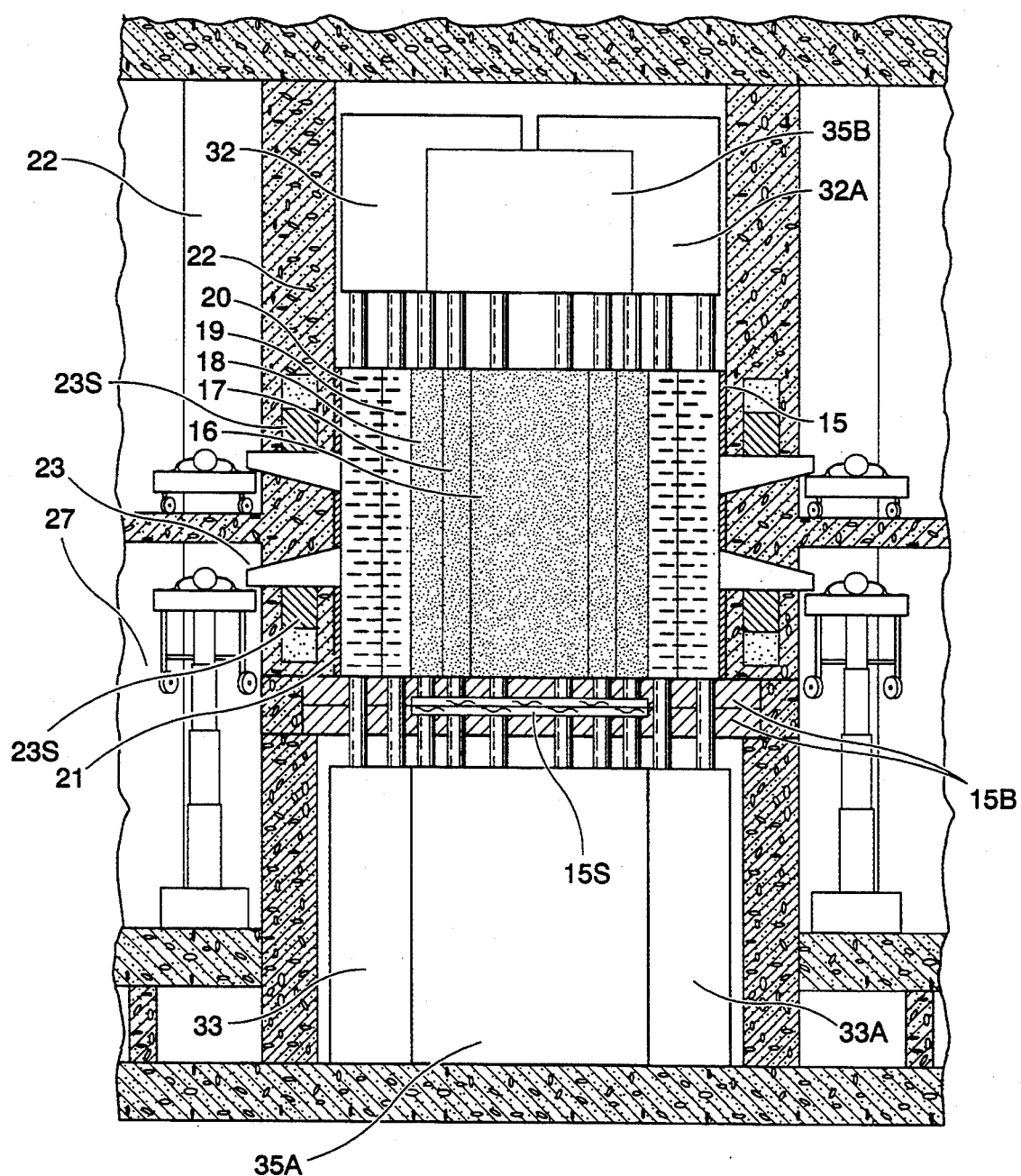

FIG. 3 illustrates patient treatment on two (2) levels, doubling the number of treatment rooms of one level. The beam tubes are both located near the reactor midplane, one pointing somewhat upward, one downward. Suitable treatment tables or chairs, move the patients up or down toward the beam tube openings.

DESCRIPTION OF THE PREFERRED EMBODIMENT

General Description

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
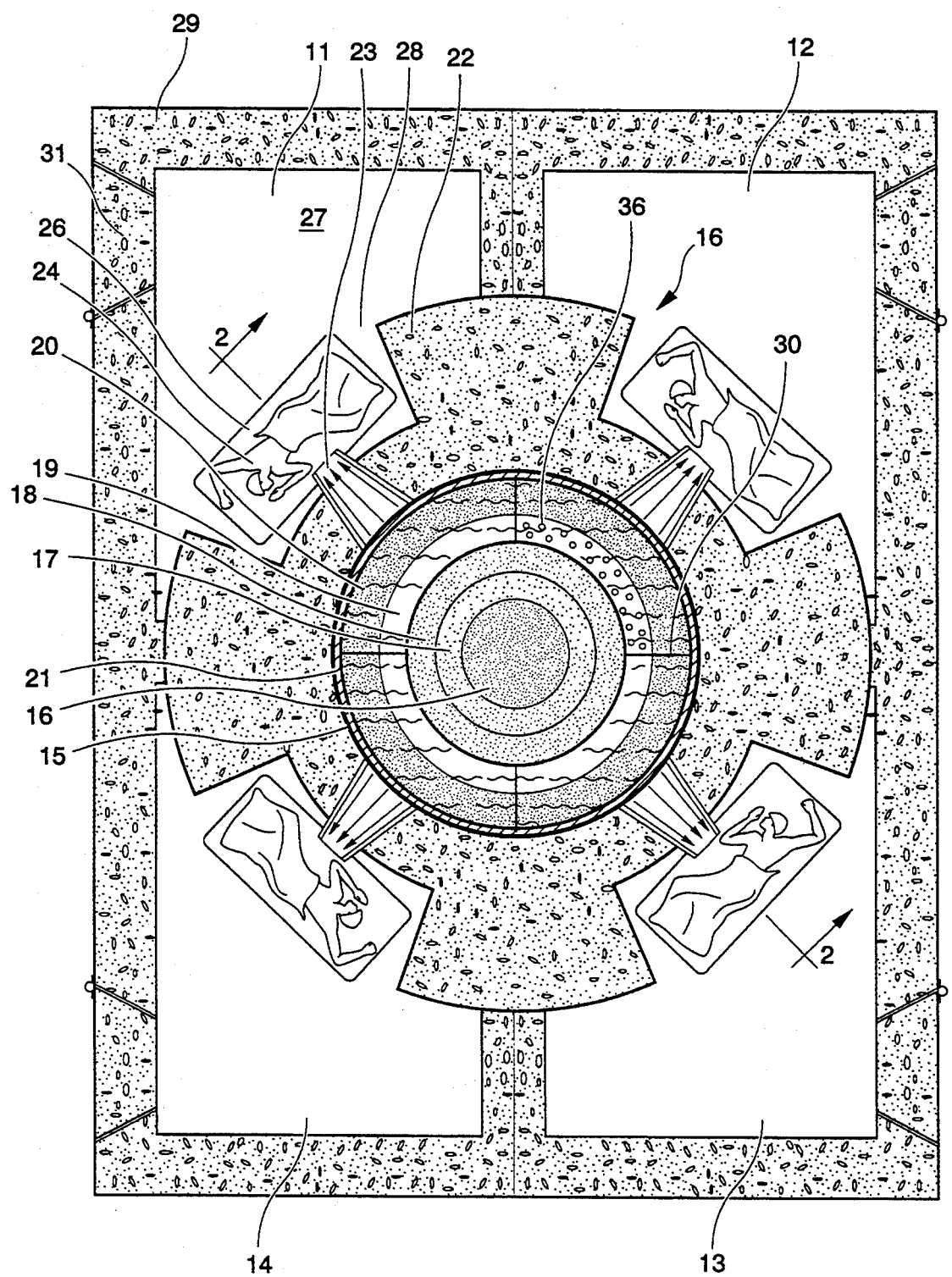
FIG. 1 is a top plan view of BNCT apparatus according to a typical embodiment of the present invention.

Referring now to the drawings in detail, FIG. 1 is a schematic plan view of a portion of a building having four treatment rooms 11, 12, 13 and 14. Since each of the rooms is essentially like the others, description of one should suffice for all. A nuclear reactor is at the center of the array of rooms and includes an inner core 16, an outer core ring 17, and a heavy metal ring 18. There are two different moderator rings 19 and 20. Reactor shielding 21 and 22 surrounds the core and moderator rings. Ring 21 is a special $\gamma$-ray shield, consisting typically of lead (Pb) or bismuth (Bi). Ring 22 is the classical biological shield of concrete. Everything within the concrete is confined in a reactor vessel 15 of stainless steel or aluminum or other material of conventional nature, so the vessel itself is shown no more specifically than by the thickness of a line 15 in the drawing. Similarly, the construction within each core and heavy metal region may be conventional, so is not shown in detail. For example, the central core may comprise bundles of fuel rods, several control rods for safety purposes, and cooling water in the interstitial portion of the core. Also, the second core region may comprise bundles of fuel rods, with cooling water in the interstitial portion of the region. The bundles may be closer together in region 17 because, according to one feature of the invention, the regions are characterized by decreasing enrichment structure of the uranium fuel.

Light water ($H_2O$) is used as coolant in all three metal regions. The cooling required for region 17 is less than for the central region 16. Still less cooling is required for the heavy metal region 18. Therefore, the third region may be primarily cast metal, with cooling water passageways through it. The cooling water is piped up through the three core metal regions and can be the same and commingle, particularly in the sealed space 15S between the central portions of the two steel reactor-supporting base plates 15B. Thus, the cooling water for all three regions of the core can be circulated through the same heat exchanger by the same pump.

The core/metal regions are surrounded by moderator/absorber regions, contained in the vessel, followed by concrete shielding. The total radius to concrete is about one meter.

A beam tube 23 through the shielding ring 22 on a radius from the core 16, permits neutron transmission to the patient 24 on a cart 26 supported on a floor 27 at the treatment station 28 in room 11. The room walls and ceiling are provided with shielding, as indicated at 29, for example. The same is true of the treatment room door 31. Vertically slidable shielding shutters 23S are normally disposed across and thereby close the beam tubes, and would be opened to the positions shown only during the short (ten minute, for example) treatment of the patient in a treatment room. Alteratively, the beam tubes could be "plugged" from the outside, instead of employing an internal shutter.

The Core/Metal Regions

The two inner regions of the nuclear reactor contain nuclear fuel. In order to have the highest macroscopic inelastic scattering cross section, in other words, to provide as much down-scattering capability for fast neutrons as possible in the smallest space, metal fuel is preferred.

To maximize the depression of the high energy wing of the spectrum and to minimize the transmission of $\gamma$-rays from nuclear fission, two fuel enrichments and a heavy metal ring are applied.

The inner-core fuel has about 20% enriched uranium, and about 30 cm radius. Most of the fission neutrons are produced in the inner core.

For the second region, the core ring 17 contains further U-metal fuel, but of a low enrichment, e.g. 4% U-235, with 96% U-238. Its thickness is typically about 15 cm.

The third region, ring 18, contains a high volume fraction of a heavy metal to provide substantial additional inelastic scattering of neutrons and more $\gamma$-ray absorption. It can be one of the non-fissionable nature. It can be depleted uranium about 0.23% U-235 in about 99.7% U-238 or it can be thorium metal as described above in the summary. Its thickness is also about 15 cm leading to a total metal region radius of about 60 cm. The energy production in this third region is very low, requiring very little cooling.

The Moderator/Absorber Regions

One of the novel features of this invention is the adjustable shaping of the neutron spectrum for an optimized treatment of tumors at various depth. The preferred embodiment employs two liquid moderator regions. The inner one contains light water ($H_2O$), the outer one heavy water ($D_2O$). In all other designs of which I am aware (see e.g. Ref. 1, pg. 333), the functions of the moderator regions are provided by special filter arrangements, employing combinations of $D_2O$, Al-metal and or $Al_2O_3$ (alumina).

The two moderator liquids ($H_2O$ and $D_2O$), are laced with "i/v-absorbers", i.e. with isotopes, such as Li-6, having a neutron absorption cross section that is largely proportional to the inverse neutron velocity, v. Lithium-6 is the widely preferred 1/v-absorber as neutron absorption in Li-6 is not followed by an emission of a $\gamma$-ray as it is in B-10, the other strong 1/v-absorber. Natural lithium can be used for simplicity. Its absorbing isotope, Li-6 has a natural abundance of about 7.5%.

The concentration of the 1/v-absorbers in the $H_2O$ and $D_2O$ rings is variable to allow special adjustment in each segment suitable for particular tumors. As the two moderating liquids are passing through coolant loops, the concentration of soluble compounds of Li may be readily changed: Pure liquid (or higher concentration liquid) may be substituted for existing solution to lower (or increase) the absorber concentration. There is sufficient time between different treatments to change the absorber concentration.

The first moderator region ($H_2O$) is about 10 to 20 cm thick, the second about 30–40 cm. The moderator regions reduce further the $\gamma$-ray flux, but most of the remaining $\gamma$'s will be absorbed by the lead or bismuth ring 21, located inside (as shown) or outside of the reactor vessel 15.

Dividing lines 30 are shown through the moderator rings in FIG. 1. Different Li concentrations may be used in the four 90° sectors of the moderator, yielding different epithermal neutron spectra. This provides a flexibility of the epithermal neutron spectrum, which should be useful for optimizing the neutron exposure for various tumors. For example, in the lower-left sector one could leave out the 1/v-absorber, thus producing a thermal neutron spectrum for skin cancer treatment. Also, 1/v-absorbers in a solid form such as plates or rods 36, for example, as shown in the upper-right sector in FIG. 1, may be employed in either of the moderator rings, along with the liquid. This could be useful if a permanent minimum 1/v-absorption capability is desired for a particular sector.

Description of the Ex-Reactor/Moderator Components

The beam tube 23 includes apparatus for collimation and possibly some additional moderation in a manner known in the art, so it need not be described further here. The beam tubes for the four different treatment rooms can be different from each other, each one optimized for a different tumor size or depth. As indicated in FIG. 1, shielding is provided around the reactor, between each treatment room and the one next to it. Depending upon the design and size of the reactor, it may be possible to have more than four treatment areas around the circumference of the reactor, possibly as much as eight or ten treatment rooms on two levels (see FIG. 3). The rooms on the lower level have lifts to raise the patient transport carts from the floor to a height where the patient on the cart is positioned adjacent the end of the beam tube for that room. Also the system can be sized for treating various sizes of animals.

Figure 2:
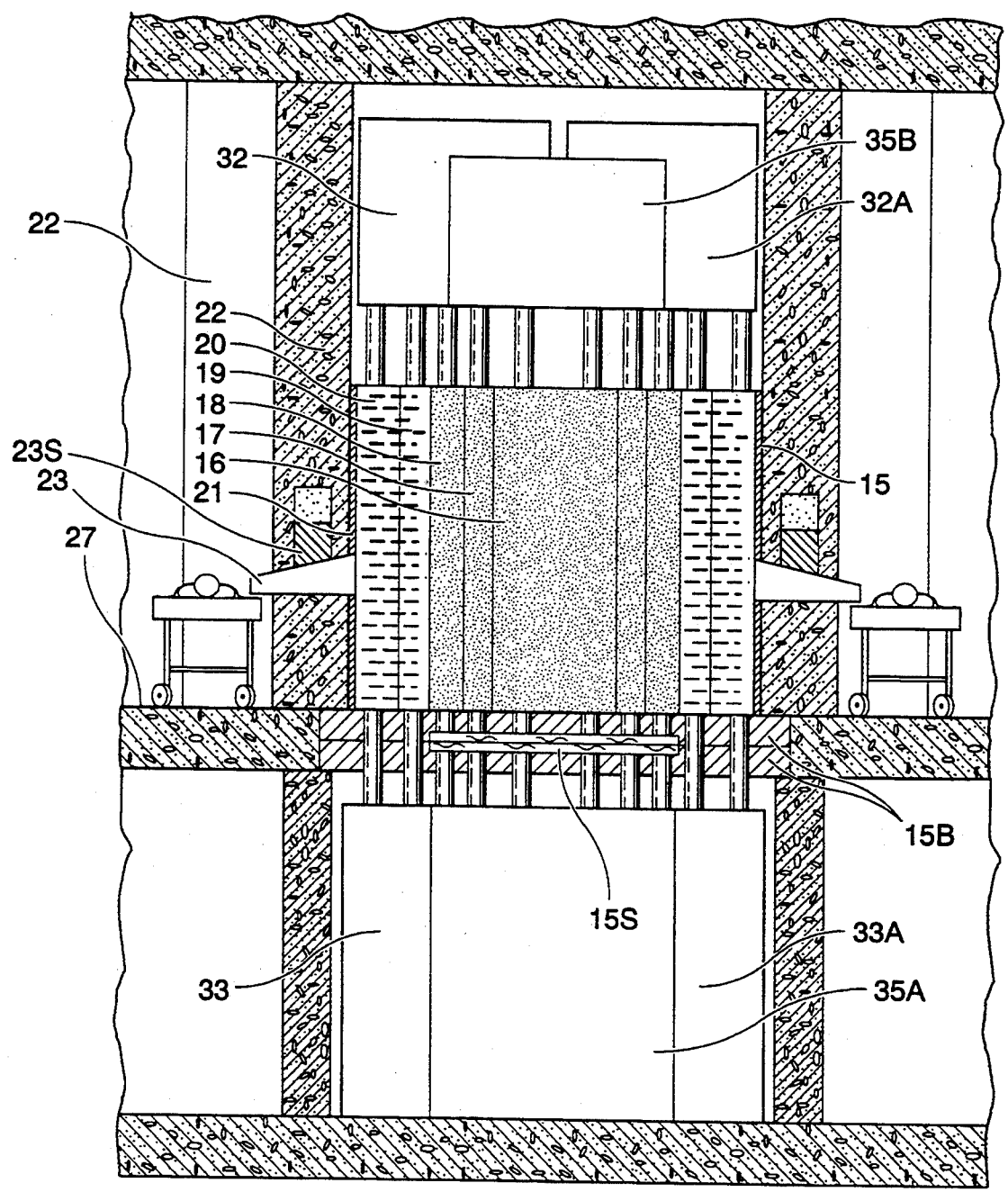
FIG. 2 is a vertical section therethrough taken at line 2—2 in FIG. 1 and viewed in the direction of the arrows.

As shown in the cross section of FIG. 2, there is piping through the reactor for each of the moderator rings and for the three core regions. These are shown entering boxes 32 at the top and 33 at the bottom which should be understood to contain appropriate fluid moving and handling pumps and heat exchangers and controls, as needed, to serve the reactor. Because those portions of the reactor on opposite sides of the four sector defining lines such as 30 are in communication with different treatment rooms, and may be designated for different treatments, they will have their own independent liquid storage, composition formulating, pump and heat exchanging equipment and valves and controls for the moderator regions, as indicated generally in the boxes 32 and 33 and 32A and 33A, while the core and heavy metal regions can share the same pump and heat exchanger for their cooling water, and have conventional controls, as indicated in boxes 35A and 35B.

PHYSICAL PRINCIPLES UNDERLYING THE INVENTION

The present invention is based upon my efforts to achieve the desired neutron energies with minimal side effects over a very short distance. The approach is different from any of which I am aware. The reasoning is as follows.

Desired Neutron Energies

The determinants for the most advantageous neutron energies in the beam are the nuclear properties of two isotopes:

The neutron capture cross section of B-10, a measure for the probability to capture a neutron; it increases with decreasing neutron velocity, v, like 1/v.

The scattering cross section of hydrogen, the most abundant constituent of human tissue; it is constant over most of the energy range, but it doubles with decreasing energy between 1 eV and energies below the mean thermal equilibrium energy (about $E_{th}=1/40$ eV).

The implications for a most effective boron-neutron-capture treatment of tumors are the following:

First, neutrons are generated by nuclear fission with energies around 1 to 2 MeV. Thus for the most efficient capture in boron they have to be "slowed down" as much as possible, i.e., to the thermal energy limit that results from the body temperature. Most of this slowing down can be accomplished already in the reactor, the rest in the moderator regions. For skin cancer (melanoma), the slowing down will have to be completed before neutrons enter the skin, e.g. in a $H_2O/D_2O$ segment without the 1/v-absorber. Neutrons will then have their best possible (lowest) energy.

Totally different is the situation for deep-seated tumors, which is the majority of tumors:

If thermal neutrons would be applied as for skin cancer, no additional slowing down could occur, but there would be considerable deflection and diffusion, primarily by the body hydrogen, to a lesser extent by oxygen, carbon and nitrogen. This would reduce substantially the fraction of beam neutrons that would reach the tumor.

Therefore, "epithermal" neutrons are generally employed in the beam, taking advantage of the lower scattering cross section of hydrogen for epithermal energies which, in the present context, may be in a range from 0.7 eV to 10 KeV and possibly up to 50 KeV. Epithermal neutrons suffer less deflection and diffusion, and a larger fraction of neutrons reaches the tumor. The residual slowing down of the neutrons will occur primarily through scattering on hydrogen on the way between the skin and the tumor.

The optimum epithermal spectrum of the impinging neutrons depends on the depth of the tumor location. Thus, special neutron spectra are desired, providing optimized beams for each location of a tumor.

Side Effects

A successful therapeutical procedure based on neutron capture requires the dose in the tumor to be considerably larger than in adjacent normal tissue. The dose in adjacent normal tissue has several components:

First, the so-called "fast neutrons", typically above 50 keV, transfer "recoil energy" in collisions with hydrogen nuclei (proton), which is subsequently lost through ionization.

Second, the $^{14}N(n,p)$ reaction with the abundant nitrogen in the tissue also produces ionizing protons.

Third, the residual $\gamma$-rays from the reactor contribute to the dose.

Fourth, most of the impinging neutrons will be absorbed in the body hydrogen with a $\gamma$-energy release of about 2.2 MeV. Of all the neutrons entering through the skin, only a miniscule fraction is absorbed in the tumor-boron. Although a fraction of the neutrons is leaking back out, the majority is absorbed in the patient. This suggests as a design criterion the minimization of the total number of neutron ($n_t$) applied to the patient. As mentioned above, this design criteria has not directly appeared in the literature. How its application influences the design will become apparent below.

A fifth contribution comes from the neutron capture in B-10 that has been deposited in normal tissue, though in lower concentration than in the tumor.

In summary, the minimization of the side effects requires a substantial reduction of the fast neutrons, of the $\gamma$-rays, and of the overall number of neutrons applied to a patient. It is desirable to reduce all five components of the side effects simultaneously.

Narrowing the Spread of the Neutron Spectrum

The neutrons produced in nuclear fission appear within a relatively broad "spectrum", mostly between 100 keV and 4 MeV, with an average energy of about 2 MeV, and a most frequent energy of about 0.7 MeV. During slowing down by elastic scattering, energy is lost in fractions of the energy before the scattering. A consequence of this is that the neutron spectrum spreads out along a logarithmic energy scale, as a constant relative energy loss (i.e. a fraction), corresponds to a constant jump on a logarithmic scale. A slowing down, say from 2.5 MeV to thermal (0.025 eV), amounts to an energy reduction by a factor of $10^8$. It is accompanied by a large spread on the logarithmic energy scale, much larger than the spread in the fission spectrum itself.

The spread of the neutron spectrum is automatically constricted again in the thermal range, where the neutrons just bounce around the mean thermal energy of 0.025 eV. Thus, for skin cancer treatment, for which one applies thermal neutrons directly, the (thermal) beam neutrons are in a relatively narrow energy range around 0.025 eV.

For deep-seated tumors, for which epithermal neutrons are applied, a beam with a wide (logarithmic) energy spread enters the patient. Apparently a wide energy spread is a disadvantage for the exposure of the tumor.

Consider the two wings of the neutron spectrum at the location of the tumor:

If the lower end of the spectrum is just the finalized along the way from the skin to the tumor, the bulk of the neutrons, and even more so the high energy wing, passes through the tumor with above thermal energies, rendering the boron neutron capture process inefficient. This suggests to narrow the low-energy wing of the spectrum as much as possible.

If alternatively also the high energy wing is thermalized by the choice of the neutron spectrum for a given distance between skin and tumor, the majority of the neutrons, and even more the low energy wing are thermalized too early, and are thus deflected and diffused before reaching the tumor, again, rendering the process inefficient. This suggests to narrow the high-energy wing of the spectrum.

Apparently, efficient neutron capture treatment by epithermal neutrons requires the epithermal neutron spectrum to be as narrow as possible, thus accomplishing the tumor treatment with the smallest overall number of neutrons in the beam ($n_t$). Therefore, according to my invention the apparatus is organized to narrow the epithermal neutron spectrum as much as possible. This is accomplished in the following way:

On the high energy end of the neutron spectrum the most efficient energy loss mechanism is inelastic scattering on heavy metals. Not only do some of the heavy metals have the highest inelastic scattering cross section of all nuclides, also the energy loss for high energy neutrons is larger than for elastic scattering even on hydrogen; e.g. neutrons of several MeV lose on average about 80 to 90% of their energy in a single inelastic collision on a heavy metal. A further advantage of inelastic scattering is that it does not spread out the neutron spectrum as much as elastic scattering, thus facilitating the desired narrowing of the neutron spectrum.

On the low energy end, but also at medium energies, say in the 1 to 50 keV range, elastic scattering on hydrogen is the most efficient slowing down mechanism with deuterium (D) holding the second place. But employing light and heavy water ($H_2O$ and $D_2O$) alone, spreads out the spectrum much more than desirable. Thus, the moderator region is laced with Li-6, using its long 1/v cross section to constrict the neutron spectrum on the down side by capturing the low energy neutrons. In the $D_2O$-region Li-6 is employed as its (n, α) reaction; no γ-rays are emitted. In the $H_2O$ region B-10 could be used. The 45 keV γ-ray, emitted after neutron capture in B-10, will be nearly completely absorbed along the way to the beam port.

Geometrical Arrangement and Optimization

The most efficient combination of the two spectrum-narrowing effects, the inelastic scattering on the high energy and the slowing down in B-10/Li-6 laced water on the low end, requires a suitable geometrical arrangement.

As the slowing down on of the high energy end needs to be done first, a high concentration of U-238 needs to be provided within the core, accomplished by the use of metal fuel. Down-scattering through the preferred inelastic scattering is then further pursued in the heavy metal ring. To continue slowing down along the shortest possible distance, these fuel/metal regions are first surrounded by a light water ($H_2O$) region 19 (FIG. 1) with or without absorber. The next ring 20 contains the Li-6 laced $D_2O$. The special fuel/metal regions, described above, followed by the two water rings with variable 1/v-absorbers represents the novel reactor design of this application.

After the moderation of neutrons is completed to the desired extent, the next task is to absorb the remaining γ-rays. For this additional γ-ray absorption, a Pb/Bi ring is a standard measure. The γ-ray absorption is then followed by beam tubes for neutron collimation.

The optimization of the geometrical arrangement is based on the following considerations:

The outer radii of the inner fuel region with about 20% enrichment and the outer fuel ring with about 4% enrichment will have to be optimized in the design calculations. Nuclear criticality is a constraint condition; the optimization itself includes minimization of the coolant volume for an adequate low power minimization of the outer fuel radius, employing possibly a fairly slender fuel region with height/diameter considerably larger than 1.00.

The heavy metal ring is followed by two moderator regions, the inner one containing light water ($H_2O$), the outer one heavy water ($D_2O$). The outer radius of the heavy metal ring and thus the inner radius of the $H_2O$ ring will be determined in the computational evaluation of the design by a suitable figure of merit (FOM), which quantifies the down scattering of fast neutrons as function of the radius. First, in the heavy metal, $FOM_{hm}(r)$ exceeds $FOM_{H2O}(r)$ but the former decreases strongly with increasing radius, more than the latter. There will therefore be a cross-over radius, $R^*$, such that $$FOM_{hm}(r) > FOM_{H2O}(r) \text{ for } r < R^*$$

$$FOM_{hm}(R^*) = FOM_{H2O}(R^*) \text{ for } r = R^*$$

and $$FOM_{hm}(r) < FOM_{H2O}(r) \text{ for } r > R^*$$

A suitable figure of merit is the energy weighted scattering source, a concept which avoids an artificial numerical definition of the lower end of the fast neutron range.

The outer radius of the $H_2O$ ring, i.e. the transition radius between the $H_2O$ and the $D_2O$ rings is also optimized; but several considerations are needed for this determination. The main three aspects are:

a. The slowing down power of $H_2O$ is about seven times larger than that of $D_2O$. This suggests to use $H_2O$ rather than $D_2O$ for the most compact design.

b. However, there is some neutron capture in hydrogen (H) in the epithermal range, though by far not as much as for thermal neutrons. Each capture releases a 2.2 MeV γ-ray. There is virtually no neutron capture in deuterons (D). This suggests not to use $H_2O$ too close to the patient, rather using $D_2O$ in an outer ring. These γ-rays are added to the residual γ's from the core. The combined γ-ray flux needs to be strongly reduced before reaching the patient. This makes the Pb/Bi γ-ray shield part of the optimization of the $H_2O/D_2O$ transition radius.

c. A third aspect, though of lesser importance, is the fact that the scattering on hydrogen (H) spreads out the low energy neutron spectrum more than the scattering on deuterons (D). As the low energy end of the neutron spectrum is reduced by the "1/v-absorbers" in $H_2O$ and $D_2O$, the concentration of these absorbers affects to some extent the optimization of the $H_2O/D_2O$ transition radius.

Maximization of the Solid Angle

Neutrons cannot be focused like light or charged particles. This requires that the solid angle represented by the neutron source as seen from the tumor has to be maximized if the power and thus the cost of the reactor has to be minimized. Maximization of the solid angle is equivalent to a minimization of the so-called "geometrical attenuation". According to my invention, the patient is as close to the reactor as possible in a compact design of the reactor neutron source.

ADVANTAGES OF THE DESIGN OF THE INVENTION

The spectrum narrowing features, outlined above, are the most unique aspect of this novel concept. The strong emphasis is on inelastic scattering, which accomplishes the needed down-scattering of fast neutrons with a minimum of spectral spread. It is important to achieve the reduction of the fast neutrons largely within the core, as subsequent elastic scattering is not as effective against fast neutrons as is inelastic scattering in U-238 and other heavy metals.

Another advantage of the high concentration of uranium in the core, and the presence of the additional heavy metal ring described above, is the strong absorption of $\gamma$-rays near their source.

The moderator rings with separate liquid circulation loops in each sector of each ring enables tailoring the absorber concentration in the moderators between the core and each treatment station for the neutron spectrum most suitable for the type and depth of the tumor treated in the particular station.

Relegating essential aspects, reduction of fast neutrons, spectrum narrowing and the absorption of $\gamma$-rays, to the reactor-fuel-metal regions, allows a relatively compact overall design. This brings the patient closer to the reactor, minimizing the geometrical neutron attenuation. This then allows the operation of the reactor with a low power which reduces the capital cost of the facility. The power being low can likely be exploited in terms of safety advantages.

In summary, the reactor concept of this application releases an epithermal neutron spectrum as it is needed for BNCT, while at the same time minimizing all side effects. The general thrust of this compact core concept is to have the desired beam quality and intensity available at the smallest possible distance from the core center, allowing an operation of the reactor at low power, which implies low cost, enhanced safety and ease of operation.

If the low power is combined with design features that allow the operator to move the reactor into a low-power stand-by mode between treatments, full power operation may only, be part of a day. Then, burn-up of the fuel will be low, and the core need not be structured in subassemblies for the purpose of easy refueling. Core compactness can be the primary guide line. If there is an application where a high degree compactness is not as important, a uranium metal fuel might not be necessary so, for example, a uranium carbide fuel would be a possibility.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Therapy apparatus comprising:
   a fast nuclear fission reactor with a reactor core as a source of fast and epithermal neutrons;
   material around the reactor core for inelastic and elastic down-scattering of fast neutrons, such material having a macroscopic inelastic neutron scattering cross section at least as large as that of metallic bismuth;
   adjustable moderators with 1/v-absorber combination to optimize epithermal neutron spectra for different tumors;
   shielding media surrounding the reactor;
   a plurality of neutron transmission passageways through said media; and
   treatment stations outside the media at the ends of the passageways.

2. The apparatus of claim 1 and further comprising:
   collimating devices in the passageways to direct epithermal neutrons from the reactor to predetermined spots at the treatment stations.

3. The apparatus of claim 1 wherein:
   the treatment stations are circularly spaced about the reactor in a horizontal plane.

4. The apparatus of claim 1 and wherein:
   the moderator-absorber combinations are liquid media within distinct sectors, and
   the liquid media are between the source and the treatment station in at least some of the sectors, the moderator-absorber combination in one sector being separate from the moderator-absorber combination in another sector.

5. The apparatus of claim 1 wherein:
   the treatment stations are circularly spaced about the source in two vertically spaced horizontal planes, and
   radiation shielding media is in the space between the planes.

6. The apparatus of claim 5 and wherein:
   human target supports are located at the stations at the lower one of the planes and include lifts to lift a patent in the treatment station to a point adjacent the end of the passageway at the treatment station.

7. The apparatus of claim 1 and wherein the nuclear reactor comprises:
   a first central core region including enriched uranium;
   a second core region in the form of a cylindrical ring around said central core region and comprising a nuclear fuel of a lower enrichment than the central core region;
   a third region in the form of a cylindrical ring around the second core region and containing a heavy metal for inelastic and elastic scattering of neutrons and for gamma ray absorption;
   a first moderator region around the third region and containing a liquid moderator; and
   a second moderator region around the first moderator region and containing a liquid moderator.

8. The apparatus of claim 7 and wherein:

the first core region contains uranium enriched to 20% or less;

the second core region contains a low enrichment uranium fuel, about 4% U-235, and about 96% U-238; and the heavy metal in the third region contains depleted uranium metal about 0.23% U-235 in about 99.77% U-238, or thorium metal.

9. The apparatus of claim 7 and wherein:

the first core region contains uranium enriched to 20% or less;

the second core region contains a low enrichment uranium fuel, about 4% U-235, and about 96% U-238; and the heavy metal in the third region is non-fissionable.

10. The apparatus of claim 7 and wherein:

the first core region has a radius of about 30 cm;

the second core region has an outer radius of about 45 cm; and the third region has an outer radius of about 60 cm.

11. The apparatus of claim 7 and wherein:

the liquid in the first moderator region is water ($H_2O$) laced with Li or boron; and the liquid in the second moderator region is $D_2O$ laced with Li or boron.

12. The apparatus of claim 11 and wherein:

the first moderator region is ring shaped and about 10 to 20 cm thick; and the second moderator region is ring shaped and about 30 to 40 cm thick.

13. The apparatus of claim 7 and further comprising:

a cylindrical gamma ray shield of a non-radioactive heavy metal surrounding the second moderator region.

14. The apparatus of claim 13 and wherein:

the radius from the center of the first core region to the outside of the gamma ray shield is about one meter.

15. A nuclear fission reactor having a core as a source of fast and epithermal neutrons, the core having a fuel therein having a macroscopic inelastic neutron scattering cross section that is characteristic of uranium metal fuel;

material around the fuel for strong inelastic downscattering of fast neutrons;

adjustable moderator with 1/v-absorber combination to optimize epithermal neutron spectra for different tumors;

shielding media surrounding the reactor;

a plurality of neutron transmission passageways extending outward through said media; and treatment stations at the ends of the passageways outside the media.

16. The apparatus of claim 15 and wherein:

the core has a center and has nuclear fuel arranged therein such that there is decreasing fissile material concentration at increasing distances from the center.

17. The apparatus of claim 16 and wherein:

the core is multi-regional including a first region at the center, a second region around the first region and a third region around the second region, the three regions having decreasing enrichment from the highest at the first region to the lowest at the third region.

18. The apparatus of claim 17 and wherein:

the first region comprises uranium enriched to about 20% U-235, the second region comprises uranium enriched to about 4% U-235; and the third region comprises a heavy metal.

19. The apparatus of claim 16 and wherein:

the moderator with absorber combination is in the reactor and includes segmented rings of liquids around the core and arranged for selectively changing the mean epithermal energy of neutrons transmitted through the passageways.

20. The apparatus of claim 19 and wherein:

the liquid in one of the rings is different from the liquid in another of the rings.

21. The apparatus of claim 20 and wherein:

the rings are sectored about the center, the liquids in the rings of one sector being separate from the liquids in the rings of another sector.

22. A method of treating a plurality of subjects with neutron-capture therapy comprising the steps of:

locating individual subjects in plurality of treatment stations around a nuclear reactor having a nuclear fuel core;

exposing the subjects to epithermal neutron emission from a fast nuclear reactor core surrounded by metal and liquid moderator regions, after narrowing the spread of the neutron energy spectrum by inelastic and elastic scattering, the elastic scattering especially in moderators combined with 1/v absorption in moderators around the metal regions.

23. The method of claim 22 and further comprising the steps of:

narrowing the spread of the neutron energy spectrum by absorbing neutrons in moderator liquid rings around the core, and using different liquid compositions in at least two of the moderator rings.

24. The method of claim 22 and further comprising the step of:

absorbing neutrons in at least one moderator liquid ring around the core.

25. The method of claim 24 and further comprising the step of:

locating the subjects at a distance between one and two meters from the core.

26. The method of claim 24 and further comprising the step of:

dividing the moderator liquid ring into sectors, and using a moderator liquid composition in one sector that is different from the composition in at least one other sector.

27. The method of claim 24 and further comprising the step of:

providing 1/v neutron absorbing material in the ring partly as solid and partly as liquid.

* * * * *